United States Patent [19]
Sukhatme

[11] Patent Number: 5,869,230
[45] Date of Patent: Feb. 9, 1999

[54] GENE TRANSFER INTO THE KIDNEY

[75] Inventor: Vikas P. Sukhatme, Newton, Mass.

[73] Assignee: Beth Israel Hospital Association, Boston, Mass.

[21] Appl. No.: 413,997

[22] Filed: Mar. 30, 1995

[51] Int. Cl.[6] .............................. A01N 1/02; C12N 15/63; A61K 48/00; C07H 21/04
[52] U.S. Cl. .................... 435/1.1; 435/172.3; 435/320.1; 514/44; 536/23.1; 424/93.2
[58] Field of Search .......................... 424/93.2; 435/61.1, 435/172.3, 235.1, 1.1, 320.1; 514/44; 536/23.1

[56] References Cited

U.S. PATENT DOCUMENTS 5,672,344   9/1997   Kelley et al. ........................... 424/93.2

FOREIGN PATENT DOCUMENTS

| 94 03151 | 3/1994 | France ............................ C12P 21/02 |
| 2 717 500 | 9/1995 | France . |
| WO 95/14082 | 5/1995 | WIPO . |

OTHER PUBLICATIONS

Urushihara et. al.. Transplantation. vol. 57 (11):1684–1686, Jul. 1, 1994.
Lim et. al.. Laboratory Investigation. vol. 83(6):2007–2001, Jun. 30, 1991.
Crystal, R., "Transfer of Genes to Humans: Early Lessons and Obstacles to Success", *Science* (1995) vol. 270: 404–410.
Randall, T., "First Gene Therapy for Inherited Hypercholesterolemia a Partial Success" *Medical News & Perspectives* (1993) vol. 269: 837–838.
Marshall. Gene therapy's growing pains. Science. vol. 269:1050–1055, Aug. 25, 1995.
Wagner et al.. In vivo gene transfer: focus on the kidney. Nephrology Dialysis Transplantation. vol. 10:1801–1807, Nov. 13, 1995.
Blaese et al.. Vectores in cancer therapy: how will they deliver? Cancer Gene Therapy. vol. 2(4):291–297, Oct. 1995.
Heikkila et al.. Adenovirus–mediated gene transfere into kidney glomeruli using an ex vivo and in vivo kidney perfusion system—first steps towards gene therapy of Alport syndrome, Gene Therapy, vol. 3:21–27, Sep. 1996.
Orkin et al. Report and recommendatins of the panel to assess the NIH investment in research on gene therapy, Dec. 7, 1995.
Guzman et al.. Efficient and selective adenovirus–mediated gene transfer into vascular neointima, Circulation. vol. 88:2838–2848, Dec. 1993.
Marberger, M. et al. (1980) "Regional Hypothermia of the Kidney Surface or Trans Arterial Perfusion Cooling a Functional Study" *J. Urol.* 124(2):179–183.
Scheinar, J. et al. (1994) "Protection of kidney cell against ischaemic damage by decreased kidney temperature" *Olomucensis Facultatis Medicae* 138:55–57 (Biosis Abstract No. 1604).

Wilkinson, G.W.G. and A. Akrigg (1992) "Constitutive and enhanced expression from the CMV major IE promoter in a defective adenovirus vector" *Nucleic Acids Research* 20(9):2233–2239.
Zhu, G. et al. (1995) "In vivo Adenovirus–Mediated Gene Transfer Into Normal and Cystic Rat Kidneys" *J. Am. Soc. Nephrol.* 6(3):891 (Abstract No. 110).
Zhu, G. et al. (1996) "In vivo adenovirus–mediated gene transfer into normal and cystic rat kidneys" *Gene Therapy* 3(4):298–304.
Akami, T. et al. (Jun. 1994) "Introduction and Expression of Human CD59 Gene in the Canine Kidney" *Transplantation Proceedings* 26(3):1315–1316.
Brezis, M. et al. (1984) "Renal Ischemia: A New Perspective" *Kidney International* 26:375–383.
Calvet, J.P. (1993) "Polycystic Kidney Disease: Primary Extracellular Matrix Abnormality or Defective Cellular Differentiation?" *Kidney International* 43:101–108.
Chang, H. et al. (1995) "Highly Efficient Adenovirus–Mediated Gene Transfer into Renal Cells in Culture" *Kidney International* 47:322–326.
Cowley, Jr., B.D. (1993) "Autosomal–Dominant Polycystic Kidney Disease in the Rat" *Kidney International* 43:522–534.
Csete, M.E. et al. (May 1994) "Adenovirus–Mediated Gene Transfer in the Transplant Setting I. Conditions for Expression of Transferred Genes in Cold–Preserved Hepatocytes" *Transplantation* 57(10):1502–1507.
Davidson, B.L. et al (Mar. 1993) "A Model System for in vivo Gene Transfer Into the Central Nervous System Using an Adenoviral Vector" *Nature Genetics* 3:219–223.
Felgner, P.L. and G. Rhodes (Jan. 1991) "Gene Therapeutics" *Nature* 349:351–352.
Jaffe, H.A. et al. (Aug. 1992) "Adenovirus–Mediated in vivo Gene Transfer and Expression in Normal Rat Liver" *Nature Genetics* 1:372–378.
Junqueira, L.C. et al. (1986) "Urinary System" in *Basic Histology* by L.C. Junqueira et al., 5th ed., Los Altos, CA: Lange Medical Publications, Ch. 20, 413–434.

(List continued on next page.)

*Primary Examiner*—James Ketter
*Assistant Examiner*—William Sandals
*Attorney, Agent, or Firm*—Fish & Richardson P.C.

[57] ABSTRACT

This invention pertains to a method of infecting an organ or a tissue other than a liver with an effective amount of a vector carrying genetic material of interest. This invention features a method of infecting kidney cells by introducing into the vasculature of a kidney a vector carrying genetic material of interest and maintaining the vector in contact with the renal vasculature for a period of time sufficient to allow infection of kidney cells with an effective amount of the vector, and under conditions which protect the kidney from ischemic damage. This method allows for infection of a significant number of renal endothelial cells. The method of the invention can be used for both in vivo and ex vivo applications.

46 Claims, 5 Drawing Sheets

OTHER PUBLICATIONS

Kaneda, Y. et al. (Jul. 1989) "Introduction and Expression of the Human Insulin Gene in Adult Rat Liver" *J. Biol. Chem.* 264(21):12126–12129.

Kaspareit–Rittinghausen, J. et al. (Sep. 1991) "Animal Model of Human Disease: Hereditary Polycystic Kidney Disease" *American Journal of Pathology* 139(3):693–696.

Kato, K. et al. (Feb. 1991) "Expression of Hepatitis B Virus Surface Antigen in Adult Rat Liver" *J. Biol. Chem.* 266(6):3361–3364.

Kitamura, M. et al. (Aug. 1994) "Gene Transfer into the Rat Renal Glomerulus via a Mesangial Cell Vector: Site–specific Delivery, In Situ Amplification, and Sustained Expression of an Exogenous Gene In Vivo" *J. Clin. Invest.* 94:497–505.

Lemarchand, P. et al. (May 1993) "In Vivo Gene Transfer and Expression in Normal Uninjured Blood Vessels Using Replication–Deficient Recombinant Adenovirus Vectors" *Circulation Research* 72(5):1132–1138.

Levine, F. and T. Friedmann (1991) "Gene Therapy Techniques" *Current Opinion in Biology* 2:840–844.

Lim, C.S. et al. (1991) "Direct In Vivo Gene Transfer Into the Coronary and Peripheral Vasculatures of the Intact Dog" *Circulation* 83:2007–2011.

March, K.L. et al. (Jan. 1995) "Pharmacokinetics of Adenoviral Vector–Mediated Gene Delivery to Vascular Smooth Muscle Cells: Modulation by Poloxamer 407 and Implications for Cardiovascular Gene Therapy" *Human Gene Therapy* 6:41–53.

Massry, S.G. and R.J. Glassock (1983) "Renal Circulation" in *Textbook of Nephrology,* vol. 1, 3rd ed., Baltimore, MD: Williams & Wilkins, Ch. 2, 45.

Miller, A.D. (Jun. 1992) "Human Gene Therapy Comes of Age" *Nature* 357:455–460.

Moullier, P. et al. (1994) "Adenoviral–Mediated Gene Transfer to Renal Tubular Cells in vivo" *Kidney International* 45:1220–1225.

Mulligan, R.C. (May 1993) "The Basic Science of Gene Therapy" *Nature* 260:926–932.

Schäfer, K. et al. (1994) "Characterization of the Han:SPRD Rat Model for Hereditary Polycystic Kidney Disease" *Kidney Inernational* 46:134–152.

Shaked, A. et al. (May 1994) "Adenovirus–Mediated Gene Transfer in the Transplant Setting II. Successful Expression of Transferred cDNA in Syngenic Liver Grafts" *Transplantation* 57(10): 1508–1511.

Tomita, N. et al. (Jul. 1992) "Direct in vivo Gene Introduction into Rat Kidney" *Biochemical and Biophysical Research Communications* 186(1):129–134.

Zhu, N. et al. (Jul. 1993) "Systemic Gene Expression After Intravenous DNA Delivery into Adult Mice" *Science* 261:209–211.

GENE TRANSFER INTO THE KIDNEY

Work described herein was supported in part by funding from the National Institute of Health, Grant numbers DK45617 and CA40046.

BACKGROUND OF THE INVENTION

The development over the past decade of methods for delivering genes to mammalian cells has stimulated great interest in the possibility of treating human disease by gene-based therapies. Gene transfer technology has advanced considerably over the past few years. Both ex vivo and in vivo gene transfers into a variety of cells and organ systems have been accomplished. In the ex vivo form of gene delivery, cells derived either from the patient or from other sources, are first generally modified outside of the body by introduction of a particular gene or genes. These cells are then re-introduced into the body, so as to achieve either local, regional or widespread distribution. In the in vivo form of gene delivery, the gene is carried in an appropriate vehicle such as a viral vector or is introduced by non-viral means such as by lipofection or direct injection into the body. The advances of in vivo gene therapy are its relative cost advantage as well as the fact that the gene can be treated as a drug.

While retroviral vectors are used primarily in ex vivo gene therapy, adenovirus based vectors are vectors of choice for in vivo gene transfer. The advantages of adenovirus therapy include: (i) ability to transfer genes with very high efficiency into many cell types without the need for cell replication; (ii) high titers of the virus are easily achievable; (iii) they can accept large DNA fragments up to approximately 8 kb; and (iv) adenoviruses are considered to be relatively safe, because most adults have in fact acquired immunity against a variety of adenoviruses and adenovirus-attenuated vaccines have been safely used in man. However, one of the major limitations is that the expression of the adenovirus is transient, lasting from several weeks to several months. This is due to the fact that DNA introduced into a cell by an adenovirus based vectors will not incorporate into the host genome. Moreover, immune response from the host can eliminate adenovirally infected cells. New generation of adenoviruses are expected to overcome the latter problem.

In spite of the major advances in the field of gene-therapy, gene transfer into the mammalian kidney has proved difficult because of the structurally complex organization of the organ and its relatively low mitotic index. Moreover, the architectural organization of the kidney is critical for proper organ function. Thus, high efficiency gene delivery to one particular cell type may be difficult to achieve. Very little literature exists on the in vivo delivery of genes into the kidney.

Tomita et al. (*Biochem. and Biophys. Res. Comm.* 186:129–134, 1992) report a method for in vivo gene transfer into the rat kidney. They utilize HVJ (Sendai virus) and liposome methodology. In this protocol, plasmid DNA and a nuclear protein are coencapsulated in liposomes and later cointroduced into cells. The reporter gene utilized in these studies was the SV40 large T antigen. The gene transfer was conducted by inserting a catheter proximal to the right renal artery with the abdominal aorta clipped distally beneath the left renal artery. The liposome suspension was injected into the kidneys. Four days after the injection of this mixture, SV40 large T antigen was detected immunohistochemically in 15% of glomerular capillary cells. The expression of the T antigen declined rapidly over the ensuing 2–3 days. Interestingly, no expression of the foreign gene was detected outside of the glomerulus. Akami et al. (*Transplantation Proceedings* 26(3):1315–1317, 1994) have used a similar HVJ-liposome complex to introduce human CD59 gene into canine kidney in vivo. They report transient and insufficient expression of the CD59 gene in the glomerular cells of the kidney.

A study by Zhu et al. (*Science* 261:209–11, 1993), reports the use of a particular cationic liposome DNA mixture to deliver genes with high efficiency into a vast number of endothelial cells in a rat. The gene transfer protocol is initiated by tail vein injection. The study reports long-term expression in almost all of the endothelial cells of the body as well as in a variety of parenchymal cell types including the lung, spleen, lymph nodes, and bone marrow. It also reports that between 25–50% of endothelial cells in the kidney are transfected, but does not provide any information on whether these endothelial cells are in glomerular or non-glomerular regions. Also, there is no indication of the duration of expression in these kidney cells.

Moullier et al. (*Kidney International* 45:1220–1225, 1994) provides a first report of an adenoviral-mediated gene transfer into a kidney in vivo. A replication deficient adenoviral vector that contained a β-gal reporter gene was selectively perfused into the renal artery or infused through a retrograde catheter into the pyelic cavity of the adult rat kidney. Transient (2–4 weeks), low levels of the β-gal expression were observed in the proximal tubular cells, when the adenoviral vector was selectively perfused via the renal artery, while expression was observed in tubular cells from the papilla and medulla when the adenoviral vector was administered by retrograde infusion. No expression was observed in the endothelial cells of the kidney.

Therefore, the need still exists for development of methods for a more efficient in vivo gene transfer into specific kidney cells.

SUMMARY OF THE INVENTION

This invention pertains to a method of infecting an organ or a tissue other than a liver with an effective amount of a vector carrying genetic material of interest.

In one aspect, this invention features a method of infecting an organ or a tissue other than a liver by introducing into the vasculature of that organ or tissue a vector carrying genetic material of interest and maintaining the vector in contact with that organ or tissue vasculature for a period of time sufficient to allow infection of said organ or tissue with an effective amount of the vector, and under conditions which protect that organ or tissue from ischemic damage. In a preferred embodiment, an organ or a tissue is protected from ischemic damage by maintaining that organ or tissue at a reduced temperature during incubation with a vector, e.g., by packing that organ or tissue on ice. In another embodiment, the organ or tissue is protected from ischemic damage by administering the vector in combination with an oxygen supplying agent. In yet another embodiment, the vector can also be administered in combination with a vasodilator, which allows one to regulate the extent and location of infection by the vector. This method will find applications both in in vivo setting, e.g., for regional infection of large blood vessels, or for a regional infection of a limb with a vector carrying genetic material of interest,or for an organ expression of a gene product prior to harvest for organ transplantation, as well as, in ex vivo transplant setting wherein a donor organ, e.g., a heart, is infected with the vector prior to transplantation into the recipient.

In another aspect, this invention features a method of infecting kidney cells by introducing into the vasculature of a kidney a vector carrying genetic material of interest and maintaining the vector in contact with the renal vasculature for a period of time sufficient to allow infection of kidney cells with an effective amount of the vector, and under conditions which protect the kidney from ischemic damage. In a preferred embodiment, the kidney is protected from ischemic damage by maintaining the kidney at a reduced temperature during incubation with a vector, e.g., by incubating the kidney on ice for substantially the period of time that the vector is maintained in contact with the vasculature. In another embodiment, the kidney is protected from ischemic damage by administering the vector in combination with an oxygen supplying agent. In yet another embodiment, the vector can also be administered in combination with a vasodilator, which allows one to regulate the extent and location of kidney cell infection. In yet a further embodiment, the vector is a virus capable of infecting non-dividing cells, e.g., the vector is a replication deficient adenovirus. This method allows for infection of a significant number of renal endothelial cells with an effective amount of the vector. For example, it allows for infection of about 5 to about 15% of the renal endothelial cells.

The method described above confers several advantages over the techniques that presently exist in the art. It allows the vector to stay in contact with the kidney cells long enough to obtain optimal infection, while at the same time overcoming the major problem of restricting blood flow for more than few minutes, that is, it successfully protects the kidney from ischemic damage. This protection is obtained by a very simple manipulation, mainly by maintaining the kidney at low temperatures or administering the vector with an agent which can supply oxygen to the oxygen-deprived cells. Secondly, by another very simple manipulation, mainly by administration of a vasodilator in combination with the vector, this method allows for direct regulation of the location and extent of infection. Therefore, this application provides a first description of significant transfer of genes in vivo into the renal vasculature and should find application both in the creation of new models of renal diseases as well as in potential therapeutic interventions in renal disease models.

DETAILED DESCRIPTION OF THE INVENTION

This invention provides a method for infection of an organ or a tissue other than a liver with an effective amount of a vector carrying genetic material of interest, without causing irreversible ischemic damage to that organ or tissue.

In a preferred embodiment, this invention provides a method for infection of kidney cells with an effective amount of a vector carrying genetic material of interest without causing ischemic damage to the kidney. The invention features the infection of kidney cells via renal vasculature. Preferably, the kidney is protected from ischemic damage by maintaining the kidney at a reduced temperature during the incubation with the vector. Alternatively, the kidney is protected from ischemic damage by administering an oxygen supplying agent in combination with the vector. Preferably, the location and extent of kidney cell infection is regulated by administration of a vasodilator in combination with the vector. Furthermore, the invention features a kidney having about 5% to about 15% of its endothelial cells infected with the vector.

As used herein, the term "infection" refers to the transfer of genetic material (e.g., DNA or RNA) of interest via a vector into cells of a mammalian organ or tissue other than a liver. Preferably, the vector is used to infect mammalian kidney cell. The genetic material of interest encodes a product (e.g., a protein polypeptide, peptide or functional RNA) whose production by kidney cells is desired. For example, the genetic material of interest can encode a hormone, receptor, enzyme or (poly) peptide of therapeutic value. Examples of genetic material of interest include but are not limited to DNA encoding cytokines, growth factors and other molecules which function extracellularly such as chimeric toxins, e.g., a growth factor such as interleukin-2 (IL-2) fused to a toxin, e.g., the pseudomonas exotoxin, dominant negative receptors (soluble or transmembrane forms), truncated cell adhesion or cell surface molecules with or without fusions to immunoglobulin domains to increase their half-life (e.g., CTLA4-Ig). For example, cells of an organ or a tissue do not express a gene product encoded by the genetic material prior to infection. Alternatively, infection of the cells of an organ or a tissue may result in an increased production of a gene product already expressed by those cells or result in production of a gene product (e.g., an antisense RNA molecule) which decreases production of another, undesirable gene product normally expressed by the cells of that organ or tissue. Generally, the genetic material encodes a gene product which is the desired gene product to be supplied to the cells of that organ or tissue. Alternatively, the genetic material encodes a gene product, which induces the expression of the desired gene product by the cells of that organ or tissue (e.g., introduced genetic material encodes a transcription factor which induces the transcription of the gene product to be supplied to the subject). Furthermore, the genetic material could simply contain nucleic acid, e.g., in the form of single stranded DNA to act as an antisense nucleotide. A genetic material infected into a cell of an organ or a tissue via a vector is in a form suitable for expression in the cell of the gene product encoded by that genetic material. Accordingly, the genetic material includes coding and regulatory sequences required for transcription of a gene (or portion thereof) and, when the gene product is a protein or peptide, translation of the gene product encoded by the genetic material. Regulatory sequences which can be included in the genetic material include promoters, enhancers and polyadenylation signals, as well as sequences necessary for transport of an encoded protein or peptide, for example N-terminal signal sequences for transport of proteins or peptides to the surface of the cell or for secretion, or for cell surface expression or secretion preferentially to the luminal or basal side. Enhancers might be ubiquitous or tissue or cell specific or inducible by factors in the local environment, e.g., inflammatory cytokines.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue. Accordingly, the term "significant number" refers to the ability of the vector to infect at least about 0.1% to at least about 15% of the renal endothelial cells. Preferably, at least about 5% to at least about 15% of the renal endothelial cells are infected. Most preferably, at least about 10% of the renal endothelial cells are infected.

As used herein the term "vector" refers to a nucleic acid molecule capable of transporting another nucleic acid to which it has been linked into cells. Preferred vectors are those capable of producing expression of nucleic acids to which they are linked. Examples of vectors that exist in the art include: plasmids, yeast artificial chromosomes (YACs) and viral vectors. However, the invention is intended to include such other forms of vectors which serve equivalent functions and which become known in the art subsequently hereto.

A preferred approach for introducing genetic material encoding a gene product into an organ or a tissue is by use of a viral vector. In this situation, the genetic material encoding the gene product is inserted into the viral genome (or a partial viral genome). The regulatory elements directing the expression of the gene product can be included with the genetic material inserted into the viral genome (i.e., linked to the gene inserted into the viral genome) or can be provided by the viral genome itself. Infection of cells with a viral vector has the advantage that molecules encoded within the viral vector, e.g., by a cDNA contained in the viral vector, are expressed efficiently in cells which have taken up viral vector nucleic acid and viral vector systems can be used in vivo. Different viral vectors which can infect not only dividing cells but also non-dividing cells of an organ or a tissue are described separately in the subsections below.

1. Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

2. Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

3. Herpesviruses: The main feature of a herpesvirus vector is that is usually replication defective and does not integrate into the host genome. It is also capable of infecting non-dividing cells.

4. Retroviruses: Defective retroviruses are well characterized for use in gene transfer for gene therapy purposes (for a review see Miller, A. D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Other viral vector systems that may have application in the subject invention have been derived from vaccinia virus, and several RNA viruses.

In addition to viral transfer methods, such as those illustrated above, non-viral methods can also be employed to infect cells of an organ or a tissue. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the genetic material of interest by the targeted cell. Exemplary gene delivery systems of this type include liposomal derived systems, poly-lysine conjugates, and artificial viral envelopes.

In a representative embodiment, genetic material of interest can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of cells can be carried out using liposomes tagged with monoclonal antibodies against, for example, the Thy-1 antigen, the cell adhesion molecule NCAM, carbohydrate antigen 125 (CA125), or any other cell surface antigen present on the tumor cells. Furthermore, liposomes can be tagged with monoclonal antibody that recognizes a specific type of a kidney cell.

The efficacy of a particular expression vector system and method of introducing genetic material into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptasepolymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product which is easily detectable and, thus, can be used to evaluate the efficacy of the system. Standard reporter genes used in the art include genes encoding β-galactosidase, chloramphenicol acetyl transferase, luciferase and human growth hormone.

The method of the invention can be used to infect an organ or a tissue other than a liver. As used herein, the term "organ or a tissue" is intended to include non-hepatic mammalian cells organized into cooperative vascularized assemblies as units performing a given function. The term also includes both normal and diseased organs or tissues. Examples of organs or tissues include: heart, blood vessels, limb, lung, and kidney.

In a preferred embodiment, the method of the invention can be used to infect kidney cells. As used herein, the term "kidney cells" is intended to include cells normally resident in a mammalian (e.g., human, canine, rat, mouse kidney cells) kidney, as well as cells that have infiltrated a diseased kidney, e.g., monocytes, macrophages, leukocytes, etc. The mammalian kidney is an exceedingly intricate structure, with at least 15 different cell types. All of the cell types found in a mature kidney, e.g., glomerular cells, mesangial cells, interstitial cells, tubular cell, endothelial cells, are intended to be encompassed by the term "kidney cells". Preferably, in a normal kidney, the kidney cells infected by the method of the invention are the renal endothelial cells of the cortex. More preferably, the kidney cells infected are the renal endothelial cells of the outer medulla, mainly endothelial cells of the inner and outer stripes of the outer medulla. In a kidney afflicted with polycystic kidney disease (PKD), the kidney cells infected by the method of the invention are the tubular cells, interstitial cells and the renal endothelial cells of the cortex. It will be apparent to the one skilled in the art that distribution of the viral infection can differ from the normal to the diseased kidney.

Furthermore, by use of a two-step approach for the vector administration, a change in a local environment can be produced which can lead to a different distribution of the genetic material of interest. For example, in a first step, an adenovirus or other vector carrying a gene for vascular endothelial growth factor (VEGF) can be introduced into a vasculature of an organ or a tissue. The VEGF receptor is expressed exclusively on endothelial cells and VEGF expression leads to a change in vascular permeability (Millauer B. (1993) *Cell* 72:835–846). By administration, 6 hours to one or two weeks later, of a second adenovirus or other vector carrying a different genetic material of interest distribution of the viral infection can be altered. It will be within one skilled in the art to determine other factors that can be used to change the regional environment of a given organ or tissue and thus regulate the location and/or extent of viral infection.

The method of the invention can be used to infect an organ or a tissue in vivo by introducing a vector carrying genetic material of interest into the vasculature of that organ or tissue. The vector can be introduced by any number of methods, each of which is familiar in the art. For instance, a pharmaceutical preparation of the vector can be introduced systemically, e.g., by intravenous injection, or the initial delivery of the vector can be more limited with introduction into the subject being quite localized. Preferably, the vector carrying genetic material of interest is injected intra-arterially via a catheter (see U.S. Pat. No. 5,328,470) or via a winged infusion set (Terumu Medical Corporation). For example, the blood flow to the kidney can be interrupted by clamping the aorta immediately under the superior mesenteric artery and above the inferior mesenteric artery. This setting selectively excludes the left kidney without interrupting the blood flow through the contralateral right kidney. The vector can than be directly infused in the aorta nearby the left renal artery using a 23 to 30-gauge needle of a winged infusion set, after the left kidney was flushed with heparinized saline. This is followed by clamping of the left renal vein and incubation of the kidney with the vector. After the incubation the blood flow is restored.

Similarly, the vector can also be introduced via a catheter which is inserted via the left common carotid artery and the thoracic aorta placing its tip proximally to the right renal artery. The blood flow is interrupted by clipping the abdominal aorta distally beneath the left renal artery. The kidneys are than flushed with saline and the suspension containing the vector is injected thorough the catheter. The blood flow is restored (Tomita et al. (1992) $Biochem.$ $Biophys.$ $Res.$ $Commun.$ 186(1):129–134).

The critical step in introducing the vector into the vasculature of an organ or tissue is to interrupt the blood flow to that organ or tissue thus allowing successful injection. Therefore, any equivalents of the methods discussed above, that are known to those skilled in the art, are intended to be included in the subject invention.

Accordingly, a vector containing genetic material of interest is injected into the vasculature of an organ or tissue in a suspension. Preferably, the vector is suspended in a pharmaceutically acceptable carrier, e.g., an acceptable diluent, e.g., saline or auto-plasma. The term "pharmaceutically acceptable carrier" as used herein refers to a material that can be co-administered with a vector carrying genetic material of interest and which allows the vector to perform its intended function (e.g., infect that organ or tissue). Any conventional media and agent compatible with the vector carrying genetic material can serve as a pharmaceutically acceptable carrier for use in the subject invention.

The method of the invention can also be used to infect an organ or a tissue ex vivo. For example, in a transplant setting, a kidney is harvested from a donor and maintained at a reduced temperature, e.g., 4° C. During cold ischemia, the method of the invention is performed ex vivo, by perfusing an allogenic or xenogenic kidney graft with a vector carrying genetic material of interest. After an incubation period at a reduced temperature, e.g., incubation times can range from 15 minutes to 1 hour, the graft is transplanted into a recipient. It will be apparent for one skilled in the art that other non-hepatic vascularized organs or tissues amenable to transplantation, e.g., a heart, can be used in the method of the invention.

A vector carrying genetic material of interest is administered in the amount sufficient to get infection of an organ or tissue. Preferably, in the case of an adenovirus, the vector is administered in the amount ranging from about $10^8$ pfu/ml to about $10^{11}$ pfu/ml. More preferably, the vector is administered in the amount ranging from about $10^9$ pfu/ml to about $10^{11}$ pfu/ml. Most preferably, from about $10^{10}$ to about $10^{11}$ pfu/ml are administered in a pharmaceutically acceptable carrier. Many methods are available in the art for determining the appropriate amount of the vector to be administered. One skilled in the art will know how to determine appropriate amounts for vectors other than adenoviruses.

In order to obtain infection of an organ or a tissue, the vector carrying genetic material of interest needs to stay in contact with the vasculature of that organ or tissue for more than about 15 minutes. Preferably, the vector is maintained within the vasculature for a period of time ranging from about 15 minutes to about 45 minutes. More preferably, the vector is maintained within the vasculature for about 30 minutes to about 1 hour. Most preferably, the vector is maintained within the vasculature for about 45 minutes. However, it has been reported that incubation times of more than 10 minutes at normal body temperature result in marked irreversible ischemic damage of that organ or tissue.

As used herein, the term "ischemic damage" refers to any morphological or functional change that results from prolonged lack of oxygen supply to a tissue or an organ due to the obstruction of blood flow to that tissue or organ. Ischemic damage can be reversible or permanent. The method of the invention allows for substantial protection of an organ or a tissue from irreversible ischemic damage such that the function performed by that organ or tissue is substantially maintained and recovers even after a prolonged restriction of blood flow to that organ or tissue. For example, in a kidney ischemic damage is characterized morphologically by changes such as necrosis of tubular cells. Functionally it is characterized by a failure of kidney filtration which can either be reversible or permanent. Accordingly, a kidney is protected from permanent ischemic damage if no more than about 5% of tubular cells show morphological changes characteristic of necrosis.

The method of the invention allows for prolonged incubation of the vector carrying genetic material of interest within the vasculature of an organ or a tissue, while protecting that organ or tissue from irreversible ischemic damage. An organ or a tissue can be protected from such ischemic damage by one of the two methods, mainly by reducing organ or tissue temperature during incubation time or by administration of the vector in combination with an oxygen supplying agent. An organ or tissue temperature can be reduced by a number of methods, each of which is familiar in the art. An organ or a tissue can be contacted with a cold reagent, e.g., ice. For example, an organ or a tissue can be perfused with cold saline prior to the injection of the vector. In addition, an organ or a tissue can be maintained at a reduced temperature by packing it on ice during incubation time. Accordingly, an organ or a tissue is maintained at a reduced temperature of about 0° C. to about 25° C. Preferably, an organ or a tissue is maintained at a reduced temperature of about 4° C.

In another embodiment the vector carrying genetic material of interest is administered in combination with an oxygen supplying agent. As used herein, the term "oxygen supplying agent" is intended to include any substance that can provide oxygen to the cells that have been deprived of oxygen by restricting blood flow to these cells. For example, oxygen supplying agents include compounds, similar to hemoglobin, which bind oxygen and can deliver oxygen to a given organ or tissue. Some examples of these compounds include modified hemoglobins, e.g., polymerized pyridoxylated hemoglobin (Sehgal, L. R. (1983) $Transfusion$ 23(2) :158–62), or fluorocarbon emulsions, e.g., Fluosol DA (Laburde, P. (1992) $Ann.$ $Pharm.$ $Fr.$ 50(5–6):250–66).

An organ or a tissue can be protected from ischemic damage by use of either of these methods alone or in combination.

Furthermore, administration of a biocompatible polyol, e.g., poloxamer 407, in combination with a virus can increase the transduction rate of the virus 10–100 times (March et al. (1995) *Human Gene Therapy* 6:41–53), thus allowing for lower total viral dosage and exposure time. In the method of the invention, the biocompatible polyol can be administered in combination with an oxygen supplying agent or at reduced temperature to provide optimal protection from damage to an organ or a tissue. It will be within one skilled in the art to realize that other biocompatible polyols can be used in the method of the present invention.

In the method of the invention, the location and extent of an infection is regulated by administration of a vasodilator in combination with the vector. Administration of a vasodilator allows the vector to infect cells of an organ or a tissue that are located at a distance from the site of injection. For example, administration of an adenovirus alone, into the renal vasculature, will result largely in the infection of cortical endothelial cells. Administration of a vasodilator, e.g., dopamine or papaverine, in combination with an adenovirus, into the renal vasculature, will result in the infection of endothelial cells of both cortex and outer medulla. Therefore, vasodilators can be used in the method of the invention to regulate location and extent of viral infection.

As used herein, the term "vasodilator" refers to any agent that can dilate vascular smooth muscles and lower peripheral vascular resistance. Many different vasodilators are commercially available. Vasodilators can be divided into agents that interact through different types of receptors or agents that directly dilate vascular smooth muscles. For example, dopamine is an agent that primarily interacts with vascular $D_1$-dopaminergic receptors, this interaction resulting in increased intracellular concentration of cAMP and vasodilation. Dopamine can be administered only by the intravenous route at concentrations ranging from about 0.5 to about 5 μg/kg/min. Preferably, the concentration can range from about 0.5 to about 0.75 μg/kg/min. Most preferably, the concentration of dopamine is at about 0.70 μg/kg/min.

In a preferred embodiment, agents that directly dilate vascular smooth muscles are intended for use in the method of the invention. For example, many different drugs that directly dilate vascular smooth muscles are presently available, including papaverine, ethaverine, isoxsuprine, nylidrin, cyclandelate, and niacin derivatives. Papaverine, for example, acts by inhibiting phosphodiesterase, thus directly relaxing smooth muscles and increasing concentrations of cAMP. Papaverine can be administered orally, intravenously or by intra-arterial injection. Dosages range from 30 to 300 mg depending of the mode of administration.

Other vasoactive agents that can exert an effect on renal blood flow are also intended for use in the method of the present invention. These vasoactive agents include: vasopressin, prostaglandin $E_2$ and $I_2$, adenosine and nitric oxide synthetase. Vasopressin is an antidiuretic hormone which exerts its effect on a kidney by interaction with two different type of receptors $V_1$ and $V_2$. The renal response to the hormone results in vasoconstriction. However, a vasodilatory action of vasopressin can be elicited when the hormone is given in the presence of a $V_1$ antagonist (Laird (1988) In: *Vasopressin: Cellular and Integrative Functions*, Raven Press, New York). This results in an increased blood flow and fall in total peripheral resistance. Vasopressin may be used in the method of the invention to allow for viral infection into the cell of inner medulla.

Prostaglandins $E_2$ and $I_2$ belong to a family of eicosanoids which are formed from certain polyunsaturated fatty acids (principally, arachidonic acid). Prostaglandins influence renal salt and water excretion by alterations in renal blood flow and by direct effect on renal tubules. $PGE_2$ and $PGI_2$ when infused directly into the renal arteries increase renal blood flow (Dunn and Hood (1977) *Am. J Physiol.* 233:F169–F184).

Adenosine functions as an autocoid and its actions are mediated by specific receptors that reside in the plasma membrane of virtually every cell (Gerlach and Becker (eds) (1987) *Proceedings of the Third International Symposium on Adenosine*, Springer-Verlag, Berlin). The major action of adenosine is to assist in maintaining a balance between the availability and the utilization of oxygen in a given region. In the kidney, the action of adenosine results in the constriction of cortical blood vessels and vasodilation of blood vessels in the medulla. Thus, agonists of adenosine can be useful in the method of the invention.

Vasodilators or other vasoactive agents can be administered, in the method of the present invention, both before an organ or a tissue is subjected to in vivo infection with a vector carrying genetic material of interest, by intravenous injection, and also at the time the vector is injected into the vasculature of that organ or tissue in combination with that vector. Vasodilator can be administered with the same pharmaceutical carrier, e.g., saline or autoplasma that the vector is introduced in.

Applications

The present invention provides a method for significant transfer of genes in vivo into the renal vasculature and should find application in the creation of new models of renal diseases, as well as in potential therapeutic interventions in renal disease models and in renal transplantation.

Renal Transplantation

One potential application of the present invention is in the treatment of a renal allograft or xenograft with an agent delivered to endothelial cells that might lead to organ tolerance or might help in the post-operative period for decreasing the incidence of early transplant rejection or function (e.g., due to acute tubular necrosis). Conceptually, either the organ could be made less immunogenic so as to reduce the number of host T cells generated and/or the endothelial cells could be altered so as to prevent the adhesion/transmigration of primed immune T-cells or killer effector T-cells (e.g., by use of IL-2-toxin fusion proteins). Moreover, genes delivered into a transplant organ, such as nitric oxide synthetase (NOS), prior to transplantation could also serve to protect the organ post transplantation. These strategies make clinical sense since it is well known that early rejection episodes and malfunction lead to a worse long-term graft survival. Therefore, prevention of acute rejection and preservation of function immediately post transplant are of particular importance. Delivery for this purpose may be straightforward: it would be possible to utilize an adenovirus vector or to transduce using lipofection a large proportion of the endothelial cells in an allograft or xenograft either in vivo (prior to or during harvest of the graft) or ex vivo (e.g., once the organ has been removed from the donor). In addition to the genes mentioned above, these vectors could carry anti-sense constructs to one or more cell adhesion molecules (involved in lymphocyte homing) or dominant negative constructs to these molecules, or antisense constructs to MHC antigens in the transplant or locally immune suppressive lymphokines such as interleukin-10 (IL-10) or viral IL-10 or chimeric toxins which would preferentially kill T-cells, e.g., IL-2 toxin fusion protein. It is also possible that one could interfere with the recognition part of the immune system by, for example, the local secretion of CTLA4-IgG fusion proteins. This list of candidate genes is not exhaustive. Those skilled in the art of transplantation know of others. The genes could be delivered with constitutive promoters or with appropriate inducible enhancers. The method of the invention could be used during or prior to the harvest of a kidney from a brain-dead patient. Clearly, safety and other issues of the adenoviruses would not be an issue since the adenovirus would be flushed out prior to or just after the removal of the kidney and prior to its subsequent transplantation into a recipient.

Renal Cancer

The largest group of renal cancers are adenocarcinomas thought to be of proximal nephron origin. The structures tend to be highly vascular and may thus be amenable to gene targeting via the circulation e.g., by selective arterial catheterization. Use of the method of the present invention could lead to the delivery of agents to destroy the tumor or its vasculature as the goal of therapy, thus obviating the need for a unilateral nephrectomy. For example, the method of the invention can be used for in vivo delivery of cytokine genes, e.g., γ-INF, IL-2 or TNF, or dominant negative constructs to antagonize locally active cytokines, e.g., VEGF dominant negative receptor construct.

Acute Tubular Necrosis (ATN)

Another potential use of the method of the present invention is for the prevention or treatment of ATN. It is possible that such therapy could be given in a prophylatic manner in certain clinical situations. For example, it may be desirable to infuse an appropriate growth factor prior to operations known to compromise renal hemodynamics. This factor could be delivered to endothelial cells in the renal artery in vivo by vectors containing the appropriate gene. Such delivery could either occur pre-operatively or perhaps be given intra-operatively. Alternatively, an agent which can maintain the original blood flow could be delivered, e.g., gene for nitric oxide synthetase (NOS). Recently, antibody to the intercellular adhesion molecule-1 (ICAM-1) has been shown to protect the kidney against ischemia in a rat model (ASN (1993) Abstract 80P, p. 738). In principle, such therapy could also be delivered via antisense oligonucleotides to ICAM-1 or dominant negative constructs.

The use of the method of the invention once either ischemic ATN or nephrotoxic ATN has set in may also be appropriate. One can speculate that delivery of an appropriate growth factor(s) may aid in the recovery process since such factor(s) may be rate limiting. Thus, infection of endothelial cells in the renal arterioles in viva with growth factor genes might provide high local concentrations without systemic toxicity.

Renal Artery Stenosis

There might be a role for the method of the invention in the prevention of renal artery restenosis following angioplasty. This problem is less well-studied in the kidney than in the coronaries but there is considerable data from coronary artery angioplasties. Events identified to date include: initial platelet aggregation on denuded endothelium, liberation of growth factor(s) such as PDGF, hyperplasia of vascular smooth muscle cells, and increased extracellular matrix production. Drug therapy directed at one or more or these steps is under investigation. The recent demonstration by Dzau et al. (Morishita et al. (1993) *Acad Sci USA* 90:8474–8478) that "post-angioplasty" application of antisense oligonucleotides to two cell-cycle regulated genes prevents re-stenosis in a rabbit carotid model is most exciting. In fact, application to the kidney may be more straightforward since the kidney can withstand a longer period of shaped catheters, e.g., those containing both distal and proximal balloons, to introduce into endothelial cells in vivo agents such as antisense oligos, or other constructs that might play a role in preventing re-stenosis.

Polycystic Kidney Disease (PKD)

The role for the method of the invention in the possible treatment for PKD might be in delivering not the PKD1 gene itself but in delivering other genes "regulated downstream" by the PKD1 gene product and which might be involved in the development of cysts. For example, an antagonist to a growth factor could be introduced by the method of the present invention. This antagonist might be able to exert an inhibitory effect, even if not expressed by every tubular cell. Successful introduction of the viral vector carrying β-gal reporter gene into the kidney of a PKD rat is described in the examples section below.

Applications to Study of Renal Development Gene Expression and Models of Renal Disease There are other applications of delivering genes to the kidney which would be of particular use in the study of kidney development in general (Sukhatme (1993) *Renal Development Challenge and Opportunity, Seminars in Nephrology* 13:422–426 and Avner (1993) *Renal Developmental Diseases, Seminars in Nephrology* 13:427–435), for example, in defining cis-regulatory elements operative in the kidney, in cell lineage analysis and in the study of models of glomerulonephritis and other kidney disorders. For example, rather than generating transgenic mice it would simpler to study the effect of cis-regulatory elements introduced in vivo using methods of the invention. Similarly, in studying a variety of models of glomerulonephritis, it would be particularly interesting to over-express one or more growth factors. Such protocols would be more controllable (temporally) and easier to attempt then generating transgenic mice. For example, kidney cells could be infected with a particular cytokine or cytokine "antagonist". This could help us address questions such as what would happen if a cytokine that can promote leukocyte migration was introduced into a kidney. Would this enhance ischemia-reperfusion injury? Other sorts of models in which the phenotype of the model can be noted over a period of 3–4 weeks may also be studied using the method of the invention, because it is expected that adenovirus expression will last over this period of time. These models of renal disease described above could also be used in development of new drugs.

Other applications for the method of the present invention are in the treatment of chronic and/or acute renal disease.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

Exemplification

Materials and Methods

Cell culture. HeLa-cells (ATCC CCL2) and 293 (ATCC CRL1573) cells were obtained from American Type Culture Collection (ATCC, Rockville, Md.). They were maintained as recommended by the ATCC.

(i) Recombinant adenovirus production

The recombinant replication deficient adenovirus (Ad.CMVβgal) encoding the *E. coli* β-gal. gene driven from a CMV promoter lacking adenoviral sequences 468 to 3328 was a kind gift from Dr. R. Crystal. This virus lacks the E1A gene and therefore, will not replicate unless it is supplied with the E1A product in trans. The construct also contains SV40 splice donor and splice acceptor sites and a polyadenylation signal. The entire construct is based on the adenovirus type 5 genome.

High titer stocks of recombinant adenoviruses were prepared by amplification in the human embryonic kidney cell line 293 (ATCC CRL1573), which constitutively expressed both the E1A and E1B genes in the genome, thereby allowing proliferation of replication-deficient adenovirus vectors, using established methods (Graham, F. L. et al. (1973) *Virology* 52:456–467). Briefly, 293 cells which contain the adenoviral E1A region were cultured in fifty 150 mm culture dishes (Corning) in DMEM (Gibco) containing 10% fetal bovine serum (Hyclone), 100 U/ml penicillin (Gibco) and 100 μg/ml streptomycin. The cells were infected with adenovirus when 90% confluent.

Infected monolayers of cells were harvested 36–48 hours post-infection and subjected to 5 rounds of freeze thawing in a dry ice/ethanol water bath. Cell debris was removed by centrifugation, 3,000 rpm for 5 minutes. The crude viral lysate was applied to a p=1.40, p=1.25 CsCl density gradient and centrifuged at 35,000 rpm for 1 hour at 12° C.

The viral band was removed from the gradient and dialyzed for 6 hours with 2 changes of buffer against 1L of 10 mm TrisCl pH 7.4, 1 mm $MgCl_2$, 10% glycerol to remove the CsCl. The virus was aliquoted and stored at −80° C.

The viral titer was determined by optical density (260 mm) and by plaque formation. In the latter case viral particles were serially diluted and incubated for 90 minutes on 293 cells. The cells were overlaid with 2 ml of 1:1, 2% SEAPLAQUE agarose (Sigma) and 2× MEM (Gibco) solution containing 15% fetal calf serum (Gibco), 2% glucose (Gibco) and 1% penstrep (Gibco) at 37° C. Five days later the cell were overlaid with a further 2 ml of the overlay solution. The plates were examined and the titer calculated according to the number of plaques formed. To ensure there was no contamination with recombinant competent Ad.CMVβgal, which may arise through random homologous recombination, this procedure was also carried out using HeLa cells (ATCC CCL2) which lack the E1A region.

(ii) In Vitro infection of HeLa cells

HeLa cells were plated onto 6 wall plates at a density of $1.5 \times 10^6$ cells per plate 24 hours prior to viral infection. Following the 24-hour incubation, the cells were washed three times with cold PBS and pre-chilled for 30 minutes. The cells were infected with 2 ml of cold (4° C.) media containing 100μ of Ad.CMVβgal ($OD_{260}$=0.159 of 1:25 dilution of viral stock) suspended in cold (4° C.) DMEM containing 10% fetal bovine serum and incubated for 15,30, 45,60,75 and 90 minutes, respectively. After each incubation period, the cells were washed three times with PBS and supplemented with DMEM containing 10% fetal bovine serum.

(iii) β-galactosidase transgene histochemistry analysis

Fourteen hours after infection cells were washed three times with cold PBS and fixed with 4% paraformaldehyde in PBS for 20 minutes at 4° C. One ml of freshly prepared substrate containing 0.4 mg/ml 5-bromo-4-chloro-3-indolyl-β-D-galactosidase (Sigma), 4 mM $K_3Fe(CN)_6$, 4 mM $K_4Fe(CN)_6$ and 2 mM $MgCl_2$ was added to each well. After a two-hour incubation period the cells were examined microscopically for β-galactosidase expression.

(iv) Infusion through the renal artery

Male Wistar rats, 250–300 g (Charles River Laboratories, Wilmington, Mass.) were anesthetized and underwent surgical exposure of the left kidney, the aorta and the left renal blood vessels. The left renal blood circulation was interrupted by clamping the aorta immediately under the superior mesenteric artery and 0.5 cm above the caudal end of the aorta. A 23-gauge needled of winged infusion set (Terumu Medical Corporation) was inserted into the aorta, slid up to the bifurcation of the left renal artery and fixed with a suture ring. The left kidney was flushed with 1.5 ml of ice-cold PBS containing 100 units of heparin within 1 minute. 100 μl of Ad.CMVβgal ($OD_{260}$ range of 0.159–0.325 of a 1:25 dilution of viral stock) was added to 600 μl of auto-plasma with or without vasodilator. Dopamine was given intravenously in the femoral vein at 0.75 μg/kg/min, half an hour before and throughout the 45 min. incubation period, and then for 20 min. post incubation. In addition dopamine was added to the virus at 0.3 μg/ml. Papaverine was added to the virus, total of 7.5 pg, in the total viral infusion volume of 700 μl (100 μl of viral stock and 600 μl of auto-plasma). Through the above infusion set, 0.3 ml of viral suspension was slowly infused into the left kidney before clamping the left renal vein, and the rest, immediately after venous clamping. The infused kidney was packed with PBS ice and incubated for 45 minutes. The needle hole in the aorta was closed with an 8-0 suture. The renal blood flow was re-established at the end of incubation.

Animals were sacrificed at various intervals from 1 to 3 days after viral infusion. The contralateral right kidney for arterial infusion served as an internal negative controls. The expression of the transferred gene was determined by β-galactosidase enzymatic cytochemistry staining. In addition, the liver and spleen were also checked for possible distribution of the infused virus.

(vi) Enzymatic cytochemistry

A β-galactosidase enzymatic cytochemistry method was used to detect transferred gene expression. After removal, both kidneys, the liver and spleen were sliced into 2–4 mm thick tissue blocks, which were then fixed in 4% paraformaldehyde in PBS on ice for 2 hours. For gross staining, the tissue blocks were washed in PBS on ice for 2 hours with 3 changes, followed by incubation at 4° C. for 24 hours with β-galactosidase substrate containing 0.4 mg/ml 5-bromo-4chloro-3-indolyl β-D-galactopyranoside (X-gal, Sigma B4252), 4 mM potassium ferrocyanide, 4 mM potassium ferrocyanide and 2 mM magnesium chloride. For frozen section staining, the tissue blocks were rinsed once in 30% sucrose-PBS solution, incubated in the same solution at 4° C. overnight, embedded in OCT compound and frozen in liquid nitrogen. Six, 12 and 18 μm thick sections were prepared, and washing in PBS at 4° C. for 5 to 10 minutes. Above substrate solution was applied to and incubated with the sections at 4° C. overnight, followed by nuclear hematoxylin counterstaining.

Results

Initial studies tested several different parameters with regard to the efficiency of adenovirus infection. It was discovered very quickly that intra-arterial injection by itself without any clamping did not lead to any β-gal activity in the kidney. Indeed, most of the activity was identified in the liver and, to a lesser extent, in the spleen, corroborating studies from others. Therefore, a series of studies was initiated in which the renal vein was clamped. Initially a saline solution was used to perfuse the kidney through the renal artery, the renal vein was then clamped and further solution of adenovirus was injected in. It was quickly realized that warm ischemia time of more than 10 minutes resulted in marked morphologic changes in the kidney suggestive of necrosis and standard ischemia-reperfusion injury resulted. Unfortunately, earlier cell culture work had indicated that incubation times of less than 10 minutes result in very low efficiency of adenovirus transfection infection. In an effort to modify this degree of damage and to allow a longer period of incubation, the question was asked as to whether adenovirus would infect kidney cells in the cold. Therefore, a series of experiments was initiated in cell culture first. HeLa cells were incubated with cold adenovirus after they had been washed with pre-chilled cold medium.

In a first series of experiments, the adenovirus was placed on the HeLa cells for varying degrees of time. The cells were then transferred to 37° with removal of the adenovirus and the medium was replaced by DMEM with 10% fetal bovine serum. After 14 hours of incubation in this medium, β-gal staining was performed. In these experiments it became quite clear (see FIG. 1) that there was a sigmoidal curve of efficiency of adenovirus infection as a function of time and that the inflection of this curve occurred roughly in the 15–45 minute range. A 15 min. incubation of the virus with the HeLa cells in the cold resulted in approximately ½ of the cells labeled as compared with what was seen after 45 min. incubation. Results at 45 min. were similar to those at 60, 75, and 90 min. all of which showed efficiency of infection of approximately 30–50%. It was reasoned, therefore, that if the same could be done in the kidney in vivo, this might be a way of getting adenovirus into the kidney vasculature more efficiently. Prior to these studies, however, a second parameter was tested, namely the time after which one could develop the blue staining after infection in the cold. With regard to this time point, it was noted that as early as 6–10 hours it was possible to detect adenovirus-mediated β-gal staining.

The first set of experiments in vivo in the cold involved the use of cold saline flushes. The details are described in the Methodology section and show that with 45 minutes of incubation of the adenovirus with a cold kidney several things were accomplished. First and most importantly, there was no or minimal evidence (less than 5% of tubular cell necrosis) of morphologic kidney damage. At 3 days after infection a marked fairly stereotypic response of ischemia-reperfusion injury would have been expected which did not occur. Therefore, the cold was able to protect the kidney from ischemia-reperfusion injury.

Immunohistochemistry techniques were used to identify blue staining (β-gal expression) in the kidney. It was clear that the larger blood vessels in the cortex, as well as the periglomerular capillaries were stained blue. This was seen both in the gross (FIG. 2) as well as in microscopic sections. Interestingly, the glomeruli and the glomerular capillary loop were not stained, but obviously virus must have passed through these in order to get to the pericapillary areas. Several rats were utilized in this protocol. On some occasions it was observed that there was somewhat of a patchier distribution in that there were regional areas of the kidney that showed more blue color than others, but in general if the kidney had been successfully blanched in the first place uniform staining was obtained. Very occasionally, there was expression of blue color in tubular cells, interstitial cells or in any glomerular, epithelial or mesangial cells, e.g., in two cells in one glomerulus out of 100 glomeruli.

Figure 1A:
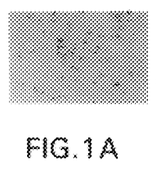
FIGS. 1A–1F. A photograph depicting HeLa cells infected with the Ad.CMVβgal adenovirus in the cold. A. refers to the 15 min. time point; B. is the 30 min. time point; C. is the 45 min. time point; D. is the 60 min. time point; E. is the 75 min. time point, and F. is the 90 min. time point. These times represent the times of incubation of the cold adenovirus with the pre-chilled HeLa cells.
Figure 1B:
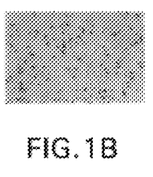
Figure 1C:
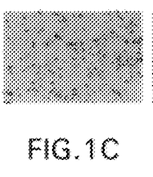
Figure 1D:
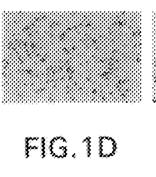
Figure 1E:
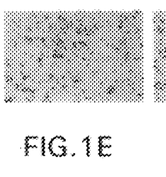
Figure 1F:
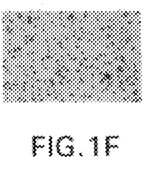
Figure 2A:
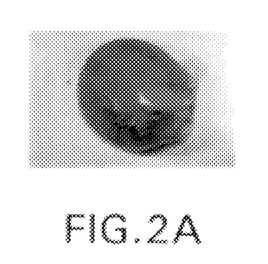
FIGS. 2A–2D. A photograph depicting gross (A, B) and microscopic (C, D) sections of a rat kidney following in vivo adenoviral transfer in the cold to the left kidney. The adenovirus (Ad.CMVβgal) was administered in autoplasma and no vasodilator was used. In A, the left injected kidney is shown. In B, the left kidney is on the left side of the figure and shows β-gal staining, while the right (control) kidney is on the right side of the figure and shows no staining. 2C and 2D are from the left kidney.
Figure 2B:
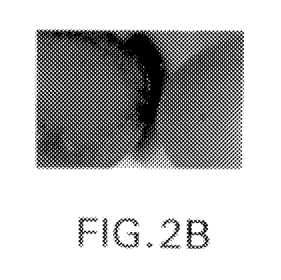
Figure 2C:
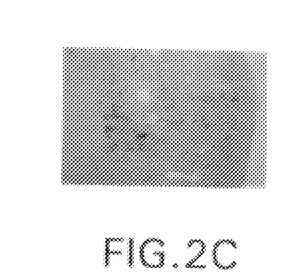
Figure 2D:
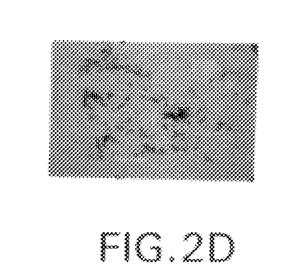
Figure 3A:
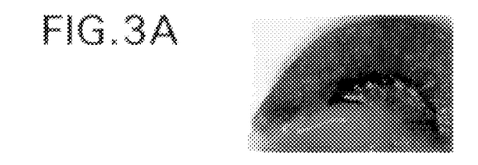
FIGS. 3A–3B. A photograph depicting sections of a rat kidney following in vivo adenoviral transfer in the cold to the left kidney. Conditions are the same as for FIG. 2 but with the use of dopamine. Gross pictures of the left kidney are shown. Note penetration into outer medulla.
Figure 3B:
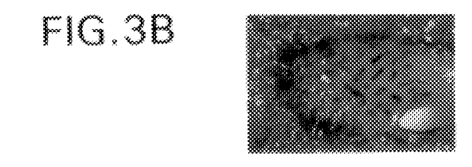

The next step was to determine whether the reporter gene can be delivered deeper into the kidney vasculature by the use of vasodilators. For these studies the animals were initially treated with intravenous dopamine and then the dopamine with the virus mixture itself was utilized. Although the staining still occurred to some extent in the cortical areas, there was now significant staining in the outer medulla, and in particular both in the inner and outer stripes of the outer medulla as can be seen both on gross and immunohistochemical sections (FIG. 3). By counting the number of blue stained endothelial cells it has been estimated that the percentage of endothelial cells transfected in these regions is approximately 10%.

Figure 4A:
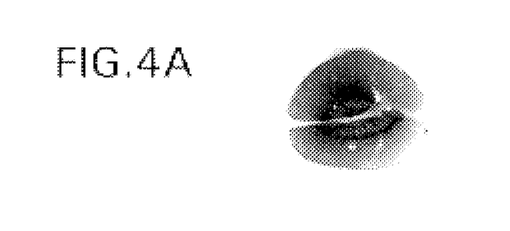
FIGS. 4A–4B. A photograph depicting sections of a rat kidney following in vivo adenoviral transfer in the cold. A. Conditions are the same as for FIG. 2 but with the use of papaverine. Note staining in the outer medulla with less staining in cortex as compared to FIG. 2. B. Left side of the figure is left kidney injected without papaverine; the right side of the figure is left kidney injected with papaverine.
Figure 4B:
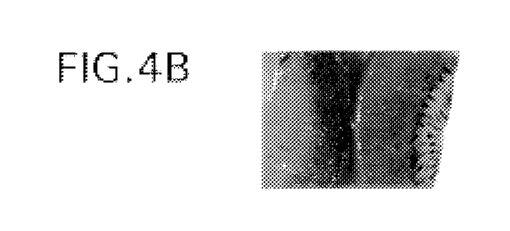
Figure 5A:
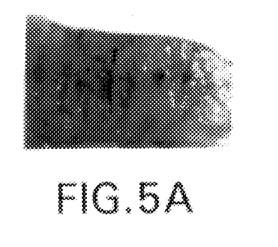
FIGS. 5A–5F. A photograph depicting sections of a kidney from a heterozygous HAN:SPRD rat following in vivo adenoviral transfer in the cold. The adenovirus (Ad.CMVβgal) was administered in autoplasma and no vasodilator was used. A. is a gross view of the left kidney. B. Shows on the left, the left kidney and on the right the right kidney (control) from the same animal. C, D, E, and F are microscopic views of the left kidney. Both C and D show cyst epithelium staining, and F shows staining of interstitial cells in addition to vascular cells.
Figure 5B:
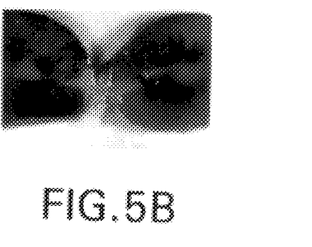
Figure 5C:
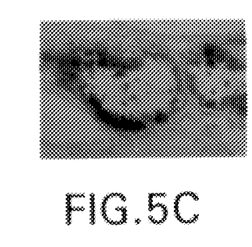
Figure 5D:
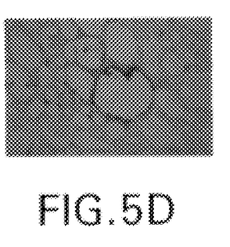
Figure 5E:
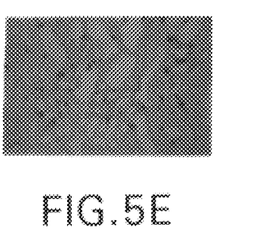
Figure 5F:
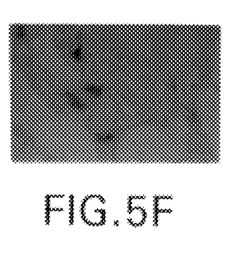

Then a second vasodilator, papaverine, was tested for ability to produce similar distribution of expression. Indeed, papaverine when used along with the virus produced data similar to the dopamine data. In general, the papaverine produced more homogeneous distribution in the kidney than the dopamine for reasons that remain unclear (FIG. 4).

Gene transfer was also tested in the HAN:SPRD rat, a model for PKD (Kaspareit-Rittinghausen et al. (1991) *Am. J. Pathol.* 139(3):693). The procedure of adenoviral infection was carried out in about 10 week heterozygous animals as detailed in the methodology section. Cold incubation time of 45 minutes was used with auto-plasma. No vasodilators were employed. FIG. 5 shows that expression of β-galactosidase activity was seen in cortical vasculature, as well as, in some interstitial cells and in an occasional cyst. These data demonstrate that gene transfer can be carried out by the methods given, to the interstitium and to the epithelium of a polycystic kidney in addition to the vasculature.

It might initially be thought that the expression of 5–15% of endothelial cells is not a significant number. However, depending on the application in question, this number can indeed be very significant. For example, it has been discovered recently by Losordo et al., (*Circulation* 89:785–792, 1994) that introduction of a β-gal reporter gene into the vasculature of a rabbit carotid artery results in approximately 0.1% of cells transduced. In this case, naked DNA or DNA liposome mixtures were utilized. However, importantly, when another reporter gene, in this case a plasmid containing a cytomegalovirus early promoter driving a human growth hormone gene was used, it was noted that at the effluent of the artery a concentration of approximately 1 ng/ml of the hormone was obtained. No detectable serum levels of hGH were obtained. These studies therefore show that a transfection efficiency of as little as 0.1% can results in very significant levels of a locally produced cytokine. With efficiencies of 5–5%, it is not inconceivable, therefore, that cytokine concentrations in the 50–150 ng/ml region might be obtainable in the kidney. The concentrations that can be obtained will clearly depend upon the half-life of the protein and RNA being made, etc., but emphasizes the point that the use of this type of delivery system in a biological system in which an autocrine or paracrine effect is required in the range of ng/ml can be achieved.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method of infecting renal endothelial cells, comprising: introducing a recombinant viral vector carrying genetic material of interest and a vasodilator into a vasculature of a kidney for a period of time sufficient to allow for infection of said renal endothelial cells with an effective amount of said vector under reduced temperature which protects said kidney from ischemic damage, wherein at least 5% of said infected endothelial cells are endothelial cells of the inner or outer medulla.

2. The method of claim 1, wherein said kidney temperature is reduced by incubating said kidney on ice.

3. The method of claim 1, wherein said vector is introduced in combination with an oxygen supplying agent.

4. An ex vivo kidney, suitable for transplantation, produced by the method of claim 1.

5. The method of claim 1, wherein said kidney is a diseased kidney.

6. The method of claim 5, wherein said diseased kidney is afflicted with polycystic kidney disease (PKD).

7. A method of infecting renal endothelial cells with genetic material of interest comprising:
   (i) restricting blood flow to and from a kidney;
   (ii) introducing into a vasculature of said kidney a recombinant viral vector carrying said genetic material of interest and a vasodilator; and
   (iii) maintaining said vector in contact with the vasculature of said kidney long enough to allow fur infection of said renal endothelial cells with said vector such that at least 5% of said infected endothelial cells are endothelial cells of the inner or outer medulla while reducing kidney temperature to a temperature such that said kidney is protected from ischemic damage.

8. The method of claim 7, wherein said vector is introduced intra-arterially or intravenously.

9. The method of claim 7, wherein said blood flow from a kidney is restricted by clamping the renal vein.

10. The method of claim 7, wherein said genetic material of interest is selected from the group consisting of cytokines, growth factors, chimeric toxins, adhesion molecules and cell surface molecules.

11. The method of claim 7, wherein the temperature of said kidney is reduced to at least about 0° C. to at least about 25° C.

12. The method of claim 7, wherein the temperature of said kidney is reduced to about 4° C.

13. The method of claim 7, wherein said kidney is incubated at a reduced temperature for at least about 30 min. to at least about 1 hour.

14. The method of claim 7, wherein said kidney is incubated at a reduced temperature for about 45 minutes.

15. The method of claim 7, wherein said vasodilator is selected from the group consisting of dopamine and papaverine.

16. The method of claim 7, wherein said vector is introduced in combination with an oxygen supplying agent.

17. The method of claim 7, wherein said blood flow to a kidney is restricted by clamping the aorta.

18. The method of claim 17, wherein said aorta is clamped under the superior mesenteric artery.

19. The method of claim 7, wherein said virus is selected from the group consisting of adeno associated-virus (AAV), adenovirus and herpesviruses.

20. The method of claim 19, wherein said replication deficient adenovirus is introduced in the amount ranging from about $10^{10}$ pfu/ml to about $10^{11}$ pfu/ml.

21. The method of claim 19, wherein said adenovirus is a replication deficient adenovirus.

22. The method of claim 21, wherein said replication deficient adenovirus is selected from the group consisting of Ad-2, Ad-3, Ad-5 and Ad-7 strain of adenoviruses.

23. The method of claim 21, wherein said replication deficient adenovirus lacks one or more of E1A, E1B or E3.

24. The method of claim 7, wherein the temperature of said kidney is reduced by contacting the kidney with a cold reagent.

25. The method of claim 24, wherein said cold reagent is ice.

26. A method of infecting renal endothelial cells with genetic material of interest comprising:
   (i) restricting blood flow to and from a kidney;
   (ii) introducing into a vasculature of said kidney a recombinant viral vector carrying said genetic material of interest and a vasodilator; and
   (iii) incubating said kidney on ice for substantially the period of time that said vector is maintained in contact with said vasculature such that at least 5% of said infected endothelial cells are renal endothelial cells of the inner or outer medulla.

27. A method of infecting renal endathelial cells in situ comprising:
   (i) restricting blood flow to a kidney by clamping the aorta;
   (ii) flushing said kidney with cold saline;
   (iii) introducing into said kidney via the renal artery an adenovirus carrying genetic material of interest and a vasodilator;
   (iv) restricting blood flow from said kidney by clamping the renal vein such that said vector is maintained in contact with the vasculature of said kidney;
   (v) reducing kidney temperature to a temperature such that said kidney is protected from ischernic damage long enough to allow for infection of said endothelial cells with said vector such that at least 5% of said infected endothelial cells are endothelial cells of the inner or outer medulla; and
   (vi) restoring blood flow to said kidney.

28. The method of claim 27, wherein said genetic material of interest is selected from the group consisting of cytokines, growth factors, chimeric toxins, adhesion molecules and cell surface molecules.

29. The method of claim 27, wherein said vasodilator is selected from the group consisting of dopamine and papaverine.

30. The method of claim 27, wherein said vector is introduced in combination with an oxygen supplying agent.

31. The method of claim 27, wherein the temperature of said kidney is reduced to at least about 0° C. to at least about 25° C.

32. The method of claim 27, wherein the temperature of said kidney is reduced to about 4° C.

33. The method of claim 27, wherein said kidney is incubated at the reduced temperature for at least about 30 min to at least about 1 hour.

34. The method of claim 27, wherein said kidney is incubated at a reduced temperature for about 45 min.

35. The method of claim 27, wherein said kidney temperature is reduced by contacting the kidney with a cold reagent.

36. The method of claim 35, wherein said cold reagent is ice.

37. The method of claim 27, wherein said kidney is a diseased kidney.

38. The method of claim 37, wherein said diseased kidney is afflicted with polycystic kidney disease (PKD).

39. A method of infecting a kidney, comprising; introducing a recombinant viral vector carrying genetic material of interest and a vasodilator to regulate the extent and location of infection into a vasculature of said kidney and maintaining said vector within the vasculature for a period of time sufficient to allow for infection of kidney cells with an effective amount of said vector under conditions which protect said kidney from ischemic damage, wherein at least 5% of said infected kidney cells are endothelial cells of the inner or outer medulla.

40. A method of claim 39, wherein the temperature of said kidney is reduced by contacting said kidney with ice.

41. The method of claim 39, wherein said kidney is incubated at the reduced temperature for at least about 30 minutes to at least about 1 hour.

42. The method of claim 39, wherein said kidney is incubated at a reduced temperature for about 45 min.

43. The method of claim 39, wherein said viral vector is selected from the group consisting of adeno associated-virus (AAV), adenovirus and herpesviruses.

44. The method of claim 43, wherein said adenovirus is a replication deficient adenovirus.

45. The method of claim 44, wherein said replication deficient adenovirus is selected from the group consisting of Ad-2, Ad-3, Ad-5 and Ad-7 strain of adenoviruses.

46. The method of claim 44, wherein said replication deficient adenovirus lacks one or more of E1A, E1B or E3.

* * * * *